US009169515B2

(12) United States Patent  (10) Patent No.: US 9,169,515 B2
Shen et al.  (45) Date of Patent: Oct. 27, 2015

(54) METHODS AND SYSTEMS FOR NUCLEIC ACID SEQUENCING VALIDATION, CALIBRATION AND NORMALIZATION

(75) Inventors: Min-Yi Shen, Palo Alto, CA (US); Douglas Greiner, Fremont, CA (US)

(73) Assignee: Life Technologies Corporation, Carlsbad, CA (US)

( * ) Notice: Subject to any disclaimer, the term of this patent is extended or adjusted under 35 U.S.C. 154(b) by 1224 days.

(21) Appl. No.: 13/030,818

(22) Filed: Feb. 18, 2011

(65) Prior Publication Data

US 2011/0207624 A1  Aug. 25, 2011

Related U.S. Application Data

(60) Provisional application No. 61/306,104, filed on Feb. 19, 2010, provisional application No. 61/438,095, filed on Jan. 31, 2011.

(51) Int. Cl.
*C12Q 1/68* (2006.01)
*B01J 8/00* (2006.01)
*C07H 21/00* (2006.01)
(Continued)

(52) U.S. Cl.
CPC .......... *C12Q 1/6874* (2013.01); *B01J 2219/005* (2013.01); *C12Q 2533/107* (2013.01); *C12Q 2535/122* (2013.01); *G01N 2201/1242* (2013.01)

(58) Field of Classification Search
CPC ........... C12Q 1/6874; C12Q 2533/107; C12Q 2535/122; G01N 2201/1242; B01J 2219/005
USPC ....................................................... 702/20
See application file for complete search history.

(56) References Cited

U.S. PATENT DOCUMENTS 5,830,645 A  11/1998  Pinkel et al.
6,040,497 A   3/2000  Spencer et al.
(Continued)

FOREIGN PATENT DOCUMENTS

EP  0304845   3/1989
EP  03300185  8/1989
(Continued)

OTHER PUBLICATIONS

Binneck, E. et al., "VSQual: a visual system to assist DNA sequencing quality control", *Genet. Mol.Res.*, vol. 3, No. 4, Dec. 30, 2004, 474-482.
(Continued)

*Primary Examiner* — Jeremy C Flinders

(57) ABSTRACT

A system for performing quality control for nucleic acid sample sequencing is disclosed. The system comprises a set of solid supports, each solid support having attached thereto a plurality of nucleic acid sequences, wherein the set comprises plural groups of solid supports and each group contains solid supports having the same nucleic acid sequences attached thereto. The nucleic acid sequences of each group differ from each other. The nucleic acid sequences are synthetically derived, and the nucleic acids sequences are designed such that the nucleic acid sequences produce a predefined pattern of detectable signals during a sequencing run. A method of preparing a quality control for performing nucleic acid sample sequencing, a method of validating a nucleic acid sequencing instrument during a nucleic acid sequencing experiment, and a method of processing nucleic acid sequencing data during a nucleic acid sequencing experiment are also disclosed.

19 Claims, 5 Drawing Sheets

(51) Int. Cl.
  *C12Q 1/48* (2006.01)
  *C07H 21/04* (2006.01)

(56) References Cited

U.S. PATENT DOCUMENTS

| | | |
|---|---|---|
| 6,261,782 B1 | 7/2001 | Lizardi et al. |
| 6,265,163 B1 | 7/2001 | Albrecht et al. |
| 6,403,315 B1 | 6/2002 | Drmanac |
| 6,492,122 B2 | 12/2002 | Weidenhammer et al. |
| 6,511,802 B1 | 1/2003 | Albrecht et al. |
| 6,620,584 B1 | 9/2003 | Chee et al. |
| 6,677,121 B2 | 1/2004 | Lizardi et al. |
| 6,818,762 B2 | 11/2004 | Rundell et al. |
| 7,226,734 B2 | 6/2007 | Chee et al. |
| 7,282,370 B2 | 10/2007 | Bridgham et al. |
| 7,341,833 B2 | 3/2008 | Rundell et al. |
| 7,510,841 B2 | 3/2009 | Stuelpnagel et al. |
| 7,563,576 B2 | 7/2009 | Chee et al. |
| 2001/0026920 A1 | 10/2001 | Chandler et al. |
| 2001/0036626 A1 | 11/2001 | Farinas et al. |
| 2002/0119484 A1 | 8/2002 | Weidenhammer et al. |
| 2003/0017484 A1 | 1/2003 | Fodor et al. |
| 2003/0224419 A1 | 12/2003 | Corcoran et al. |
| 2004/0101869 A1 | 5/2004 | Berg et al. |
| 2004/0185483 A1 | 9/2004 | Stuelpnagel et al. |
| 2005/0064406 A1 | 3/2005 | Zabarovsky et al. |
| 2005/0181440 A1 | 8/2005 | Chee et al. |
| 2005/0191698 A1 | 9/2005 | Chee et al. |
| 2005/0244870 A1 | 11/2005 | Chee et al. |
| 2006/0004526 A1 | 1/2006 | Hadd et al. |
| 2006/0110733 A1 | 5/2006 | Toohey et al. |
| 2006/0121491 A1 | 6/2006 | Wolber et al. |
| 2006/0154234 A1 | 7/2006 | Winther et al. |
| 2007/0082358 A1 | 4/2007 | Fuerst et al. |
| 2007/0190557 A1 | 8/2007 | Glover |
| 2007/0231824 A1 | 10/2007 | Chee et al. |
| 2008/0003571 A1 | 1/2008 | McKernan et al. |
| 2008/0120079 A1 | 5/2008 | Emler |
| 2008/0194414 A1 | 8/2008 | Albert et al. |
| 2008/0262747 A1 | 10/2008 | Kain et al. |
| 2009/0062129 A1 | 3/2009 | McKernan et al. |
| 2009/0181385 A1 | 7/2009 | McKernan et al. |
| 2010/0129810 A1 | 5/2010 | Greiner et al. |

FOREIGN PATENT DOCUMENTS

| | | |
|---|---|---|
| EP | 0392546 | 10/1990 |
| EP | 1953241 | 8/2008 |
| WO | WO-96/27025 | 9/1996 |
| WO | WO-98/31836 | 7/1998 |
| WO | WO-99/60170 | 11/1999 |
| WO | WO-01/14589 | 3/2001 |
| WO | WO-02/18655 | 3/2002 |
| WO | WO-2004/024949 | 3/2004 |
| WO | WO-2005/068656 | 7/2005 |
| WO | WO-2007/106509 | 9/2007 |
| WO | WO-2007/123744 | 11/2007 |
| WO | WO-2010/028366 | 3/2010 |
| WO | WO-2011/103467 | 8/2011 |

OTHER PUBLICATIONS

PCT/US09/056225, International Preliminary Report on Patentability mailed Mar. 17, 2011.

PCT/US2011/025486, International Search Report and Written Opinion mailed on Nov. 21, 2011.

Brenner, Sydney et al., "Gene expression analysis by massively parallel signature sequencing (MPSS) on microbead arrays", *Nature Biotechnology*, vol. 18, 2000, 630-634.

Brenner, Sydney et al., "In vitro cloning of complex mixtures of DNA on microbeads: Physical separation of differentially expressed cDNAs", *PNAS*, vol. 97, No. 4, 2000, 1665-1670.

EP09812376.3, Supplemental European Search Report, mailed on May 7, 2012.

Gunderson, Kevin et al., "Decoding Randomly Ordered DNA Arrays", *Genome Research*, 14: 2004, 870-877.

Shen, Richard et al., "High-throughput SNP genotyping on universal bead arrays", *Mutation Research*, 573:2005, 70-82.

Wilson, Wendy et al., "A multiplexed PCR-coupled liquid bead array for the simultaneous detection of four biothreat agents", *Molecular and Cellular Probes*, 19:2005, 137-144.

CN200980134764.7, First Search Report mailed Nov. 16, 2012 (Translation).

PCT/US2009/056225 International Search Report and Written Opinion Mailed on Apr. 12, 2010.

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Exemplary control identification sequence

<400> SEQUENCE: 1
```

```
ccaagggagg actgatcc                                              18

<210> SEQ ID NO 2
<211> LENGTH: 36
<212> TYPE: DNA
<213> ORGANISM: Artificial Sequence
<220> FEATURE:
<223> OTHER INFORMATION: Exemplary control identification sequence

<400> SEQUENCE: 2
ccaagggagg actgatccgc cttggccgta cagcag                          36
```

METHODS AND SYSTEMS FOR NUCLEIC ACID SEQUENCING VALIDATION, CALIBRATION AND NORMALIZATION

TECHNICAL FIELD

The present teachings relate to deterministic nucleic acid sequence controls used for the validation, calibration, and normalization of nucleic acid sequencing instrumentation and data.

SEQUENCE LISTING

This application contains a Sequence Listing, which has been submitted in ASCII format via EFS-Web and is hereby incorporated by reference in its entirety. Said ASCII copy is named LT00155_ST25.txt, was created on Mar. 11, 2015, and is 860 bytes in size.

INTRODUCTION

Upon completion of the Human Genome Project, the focus of the sequencing industry has shifted to finding higher throughput and/or lower cost sequencing technologies, sometimes referred to as next generation sequencing technologies. In making sequencing higher throughput and/or less expensive, the goal is to make the technology more accessible for sequencing. These goals can be reached through the use of sequencing platforms and methods that provide sample preparation for larger quantities of samples of significant complexity, sequencing larger numbers of complex samples, and/or a high volume of information generation and analysis in a short period of time. Various methods, such as, for example, sequencing by synthesis, sequencing by hybridization, and sequencing by ligation are evolving to meet these challenges.

Disadvantages that can occur in next generation sequencing techniques include increases in system noise and performance variation across the sequencing process and/or in individual steps. At each step, system noise and/or performance variation for that step can be contributed from a variety of sources, including, for example, hardware, chemistry, and software. Defects and variation relating to instrumentation, workflow, signal processing, and/or the sample can lead to poor system performance for any or all steps from sample preparation to sequence determination. Noise and variation can also prevent or hinder comparison and normalization of data sets generated over time.

Libraries of fragments created from a well-characterized naturally-occurring sample nucleic acid, such as, for example, a strain of *E. coli*, can provide data useful for evaluating noise and performance variation. However, naturally occurring samples can exhibit variation due to a variety of factors, such as mutations within individual strands of the sample, differing sequences being introduced within a desired monoclonal population of control sequences. Other controls systems and techniques are designed for use before or after a sequencing run. In some such cases, therefore, an entire sequencing run must be performed before the validity of the instrument and/or data can be determined, which can consume both materials and time.

SUMMARY

The present disclose relates to control systems, methods, and compositions for genetic analysis methods and instruments, including sequencing methods and instruments. In some aspects, the disclosure provides systems, methods, and compositions for determining and characterizing various sources of system noise and/or degradation of performance. Determination and characterization of various sources of system noise and/or degradation of performance can occur before, during, or after the performance of an analysis or individual steps or groups of steps of an analysis. Systems, methods, and compositions disclosed herein can, in some embodiments, provide consistency in sequence determination, including, for example, providing control systems, methods, and compositions that can be used to monitor and enhance instrument performance. Monitoring and enhancing instrument performance can be applied run-to-run, as well as instrument-to-instrument. Systems, methods, and compositions disclosed herein can, in some embodiments, detect and reduce the potential for performance variation and/or noise during sequencing that is due to various factors, such as chemistry and/or library construction, and thereby permit such performance variation to be attributed to instrument quality.

Figure 1:
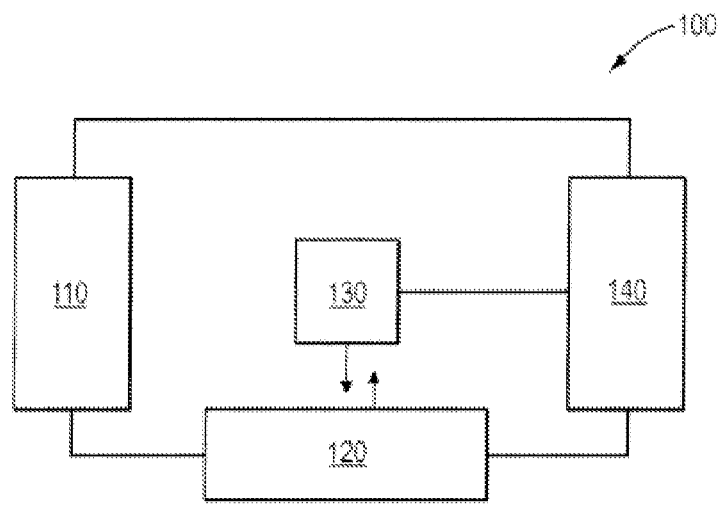
FIG. 1 depicts a block diagram representing various embodiments of instrumentation used for next generation sequencing.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts.

DESCRIPTION OF VARIOUS EMBODIMENTS

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teachings, such that slight and insubstantial deviations are within the scope of the present teachings. In this application, the use of the singular includes the plural unless specifically stated otherwise.

Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

Unless otherwise defined, scientific and technical terms used in connection with the present teachings described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques described herein are those well known and commonly used in the art.

As utilized in accordance with the embodiments provided herein, the following terms, unless otherwise indicated, shall be understood to have the following meanings:

The phrase "next generation sequencing" refers to sequencing technologies having increased throughput as compared to traditional Sanger- and capillary electrophoresis-based approaches, for example with the ability to generate hundreds of thousands of relatively small sequence reads at a time. Some examples of next generation sequencing techniques include, but are not limited to, sequencing by synthesis, sequencing by ligation, and sequencing by hybridization. Some relatively well-known next generations sequencing methods further include pyrosequencing developed by 454 Corporation, the Solexa system, and the SOLiD (Sequencing by Oligonucleotide Ligation and Detection) developed by Applied Biosystems (now Life Technologies, Inc.).

The phrase "sequencing run" refers to a sequencing experiment performed to determine the sequence of at least one nucleic acid molecule.

The phrase "ligation cycle" refers to a step in a sequence-by-ligation process where a probe sequence is ligated to a primer or another probe sequence.

The phrase "color call" refers to an observed dye color that results from the detection of a probe sequence after a ligation cycle of a sequencing run. Similarly, other "calls" refer to the distinguishable feature observed.

The phrase "synthetic bead" or "synthetic control bead" refers to a bead having multiple copies of synthetic template nucleic acid molecules attached to the bead. A linker sequence can be used to attach the synthetic template to the bead.

The phrase "fragment library" refers to a collection of nucleic acid fragments, wherein one or more fragments are used as a sequencing template. A fragment library can be generated, for example, by cutting or shearing a larger nucleic acid into smaller fragments. Fragment libraries can be generated from naturally occurring nucleic acids, such as bacterial nucleic acids. Libraries comprising similarly sized synthetic nucleic acid sequences can also be generated to create a synthetic fragment library.

The phrase "mate-pair library" refers to a collection of nucleic acid sequences comprising two fragments having a relationship, such as by being separated by a known number of nucleotides. Mate pair fragments can be generated by cutting or shearing, or they can be generated by circularizing fragments of nucleic acids with an internal adapter construct and then removing the middle portion of the nucleic acid fragment to create a linear strand of nucleic acid comprising the internal adapter with the sequences from the ends of the nucleic acid fragment attached to either end of the internal adapter. Like fragment libraries, mate-pair libraries can be generated from naturally occurring nucleic acid sequences. Synthetic mate-pair libraries can also be generated by attaching synthetic nucleic acid sequences to either end of an internal adapter sequence.

The phrase "synthetic nucleic acid sequence" and variations thereof refers to a synthesized sequence of nucleic acid. For example, a synthetic nucleic acid sequence can be generated or designed to follow rules or guidelines. A set of synthetic nucleic acid sequences can, for example, be generated or designed such that each synthetic nucleic acid sequence comprises a different sequence and/or the set of synthetic nucleic acid sequences comprises every possible variation of a set-length sequence. For example, a set of 64 synthetic nucleic acid sequences can comprise each possible combination of a 3 base sequence, or a set of 1024 synthetic nucleic acid sequences can comprise each possible combination of a 5 base sequence.

The phrase "control set" refers to a collection of nucleic acids each having a known sequence and physical properties wherein there is a plurality of differing nucleic acid sequences. A control set can comprise, for example, nucleic acids associated with a solid support. In some embodiments a control set can comprise a set of beads having a number of nucleic acid sequences attached thereto. Control sets can also comprise a solid support having a collection of nucleic acids attached thereto, such that each of the differing nucleic acids sequences is located at a substantially distinct location on the solid support, and sets of solid supports each having a substantially uniform set of nucleic acids associated therewith. The source of the nucleic acid sequences can be synthetically derived nucleic acid sequences or naturally occurring nucleic acid sequences. The nucleic acid sequences, either naturally occurring or synthetic, can be provided, for example, as a fragment library or a mate-pair library, or as the analogous synthetic libraries. The nucleic acid sequences can also be in other forms, such as a template comprising multiple inserts and multiple internal adapters. Other forms of nucleic acid sequences can include concatenates.

The phrase "deterministic transition" and variations thereof refer to the transition of color calls between ligation cycles of a sequencing run, such as, for example, a color transition, that is a predefined, predictable, and/or expected transition. For example, for a control set having deterministic color transitions, the color transitions for each nucleic acid sequence are known, e.g., a second color call of a sequencing ligation cycle can be predicted from the first color call of a sequencing ligation cycle. Conversely, a "non-deterministic transition" is a transition that is not predefined or expected. A non-deterministic color transition, for example, can comprise a first color call followed by a second color call, where the second color call cannot be predicted from the first color call.

The phrases "deterministic control set," "deterministic synthetic beads," and variations thereof refer to control sets or synthetic beads comprising synthetic nucleic acid sequences that are designed to have deterministic transitions.

The term "subset" refers to a grouping of synthetic nucleic acid sequences by a common characteristic, such as, for example, a rule of deterministic color transitions. For example, a subset can comprise all of the synthetic nucleic acid sequences in a control set that exhibit the same color call in a first ligation cycle.

The term "template" and variations thereof refer to a nucleic acid sequence that is a target of nucleic acid sequencing. A template sequence can be attached to a solid support, such as a bead, a microparticle, a flow cell, or other surface or object. A template sequence can comprise a synthetic nucleic acid sequence. A template sequence also can include an unknown nucleic acid sequence from a sample of interest and/or a known nucleic acid sequence.

The phrase "template density" refers to the number of template sequences attached to each individual solid support.

The phrase "control identification sequence" refers to a known nucleic acid sequence that can be used to distinguish between nucleic acid sequences of the control set and nucleic acid sequences of a sample, such as a target nucleic acid sequence that is the subject of nucleic acid sequencing. A control identification sequence can comprise a synthetic or natural nucleic acid sequence, and can comprise DNA, RNA, or other nucleic acids and/or derivatives. In a sequencing experiment, the control identification sequence can along with the target nucleic acid and then parsed algorithmically during processing of the sequencing data. The control identification sequence can be used to exclude nucleic acids of the control set from a set of target nucleic acid sequences.

Provided herein are various exemplary embodiments of methods, systems, and compositions for quality control in performing nucleic acid sequencing. For example, in some aspects control compositions and systems can include deterministic synthetic beads or deterministic control sets, and can be used as a control for the validation, calibration, and/or normalization of instrumentation, chemistry (e.g., probe chemistry), methods, process, and compositions used in genetic analysis. Naturally-occurring nucleic acid sequences can also be used, for example by capturing or purifying naturally-occurring molecules having sequences that are suitable for use according to the various methods and systems described herein. In some aspects the present teachings can relate to methods, systems, and compositions for validating, calibrating, and/or normalizing instrumentation used in genetic analysis.

Various embodiments relate to systems for performing quality control for nucleic acid sample sequencing. For example, a system for performing quality control for nucleic acid sample sequencing can comprise a set of solid supports, each solid support having attached thereto a plurality of nucleic acid sequences. The set of solid supports can comprise plural groups of solid supports, and each group can contain solid supports having the same nucleic acid sequences attached thereto. In some cases, the nucleic acid sequences of each group can differ from each other. The nucleic acid sequences can be naturally-occurring or synthetically derived, or both, and can produce, or be designed, engineered, or otherwise assembled to produce, a predefined pattern of detectable signals during a sequencing run. Naturally-occurring nucleic acids for use in various embodiments can be selected, isolated, and assembled according to various methods well-known in the art. As an example, suitable naturally-occurring nucleic acids can be hybridized to capture oligonucleotides and then isolated and assembled for use in various embodiments described herein. The capture oligonucleotides can be designed or generated to hybridize to nucleic acid sequences suitable for use in various embodiments.

Some exemplary embodiments of the present teachings relate to methods of preparing a quality control for performing nucleic acid sample sequencing. For example, a method of preparing a quality control for performing nucleic acid sample sequencing can comprise generating a plurality of synthetic nucleic acid sequences. Each synthetic nucleic acid sequence can differ from another nucleic acid sequence, and the plurality of synthetic nucleic acid sequences can produce, or be designed or engineered to produce, a predefined pattern of detectable signals during a sequencing reaction, process or instrument run. Methods can include, in some embodiments, attaching synthetic nucleic acid sequences to solid supports in plural groups of solid supports. The solid supports in each group can have the same synthetic nucleic acid sequence attached thereto. Each group of solid supports can be combined with the synthetic nucleic acid sequences attached to create a control set of solid supports for use in nucleic acid sample sequencing.

Some embodiments of the present teachings relate to methods of validating a nucleic acid sequencing reaction, component set, vessel, or instrument during a nucleic acid sequencing reaction, process or experiment. In some aspects, for example, methods of validating can comprise placing a set of solid supports each having a plurality of synthetic nucleic acid sequences attached thereto in a detection area of a nucleic acid sequencing reaction, vessel, or instrument. The set of solid supports can comprise plural groups of solid supports that can each have the same synthetic nucleic acid sequences attached thereto. The synthetic nucleic acid sequences can produce, or be designed or engineered to produce, a predefined pattern of observable signals during the nucleic acid sequencing reaction, process, or experiment. In some embodiments, the method can include some or all of the following steps: placing a nucleic acid sample to be sequenced in a detection area of the nucleic acid sequencing reaction, vessel, or instrument, performing a ligation cycle to attach dye-labeled probe sequences to the nucleic acid sequences attached to the solid supports and to the nucleic acid sample, detecting the dye-labeled probes attached to each of the nucleic acid sequences and the nucleic acid sample, and comparing the detected dye-labeled probe attached to the nucleic acid sequences with the predefined pattern of detectable signals to determine if the instrument and related reactions, processes, and compositions are functioning validly. Valid functioning can be assessed in a variety of ways and based on a variety of factors. As one example, valid functioning can be assessed on the basis of predefined parameters.

Various embodiments of the present teachings also relate to methods of processing nucleic acid sequencing data during a nucleic acid sequencing reaction, process, or experiment. Methods for processing data can comprise placing a set of solid supports each having a plurality of synthetic nucleic acid sequences attached thereto in a detection area of a nucleic acid sequencing reaction, vessel, or instrument. The set of solid supports can comprise plural groups of solid supports that each can have the same synthetic nucleic acid sequences attached thereto. The synthetic nucleic acid sequences can produce, and/or be designed or engineered to produce, a predefined pattern of observable signals during the nucleic acid sequencing reaction, process, or experiment. The methods can further include some or all of the following steps: placing a nucleic acid sample to be sequenced in a detection area of the nucleic acid sequencing reaction, vessel, or instrument, performing a first ligation cycle to attach dye-labeled probe sequences to the nucleic acid sequences attached to the solid supports and to the nucleic acid sample, detecting the dye-labeled probes attached to each of the nucleic acid sequences and the nucleic acid sample after the first ligation cycle, performing a second ligation cycle to attach a dye-labeled probe sequences to the nucleic acid sequences attached to the solid supports and to the nucleic acid sample, detecting the dye-labeled probes attached to each of the nucleic acid sequences and the nucleic acid sample after the second ligation cycle, comparing an intensity of the detected dye-labeled probes attached to the nucleic acid sequences after the first ligation cycle with an intensity of the detected dye-labeled probes attached to the nucleic acid sequences after the second ligation cycle, and adjusting an intensity of the detected dye-labeled probes attached to the nucleic acid sample after the second ligation cycle based on the compared intensities.

In some embodiments, the present teachings relate to a system for performing quality control for nucleic acid sample sequencing. A system for performing quality control for nucleic acid sample sequencing can comprise, for example, a solid support having attached thereto a plurality of nucleic acid sequences. The plurality of nucleic acid sequences are arranged in a set of distinct locations, wherein the set of distinct locations comprises plural groups of locations. Each group can contain locations having the same nucleic acid sequences attached thereto, wherein the nucleic acid sequences of each group can differ from each other. The nucleic acid sequences can be synthetically derived, and the nucleic acid sequences can produce, and/or be designed or engineered to produce, a predefined pattern of detectable signals during a sequencing run.

In some aspects, embodiments of the present teachings can relate to methods comprising placing a solid support having a plurality of synthetic nucleic acid sequences attached thereto in a detection area of a nucleic acid sequencing reaction, vessel, or instrument. The plurality of nucleic acid sequences can be arranged in a set of distinct locations, wherein the set of distinct locations can comprise plural groups of locations that each have the same synthetic nucleic acid sequences attached thereto. The synthetic nucleic acid sequences can produce, or be designed or engineered to produce a predefined pattern of observable signals during the nucleic acid sequencing reaction, process, or experiment. The method can include performing a sequencing cycle to attach dye-labeled probes to the nucleic acid sequences, detecting the dye-labeled probes attached to each of the nucleic acid sequences, and comparing the detected dye-labeled probe attached to the nucleic acid sequences with the predefined pattern of detectable signals to determine if the reaction, vessel, set of components, and/or instrument is functioning within predefined parameters.

In the various examples and embodiments described herein, the deterministic synthetic control systems and methods are described with regard to sequencing-by-ligation systems using two-base, or dibase, encoding (e.g., as employed in SOLiD sequencing). However, as one skilled in the art would readily appreciate, the deterministic transition scheme and methods described herein can be applied to other sequencing systems or detection techniques with some modifications as may be needed. The principles of deterministic synthetic control beads and methods using the deterministic synthetic beads can be applied to other systems and methods without departing from the scope of the present teachings as described herein and the appended claims.

Various embodiments of platforms for next generation sequencing can include components as displayed in the block diagram of FIG. 1. According to various embodiments, instrument 100 can include a fluidic delivery and control unit 110, a sample processing unit 120, an optical unit 130, and a data acquisition, analysis and control unit 140. Various embodiments of instrumentation, reagents, libraries and methods used for next generation sequencing are described in U.S. Patent Application Publication No. 2007/066931 (Ser. No. 11/737,308) and U.S. Patent Application Publication No. 2008/003571 (Ser. No. 11/345,979) to McKernan, et al., which applications are incorporated herein by reference. Various embodiments of instrument 100 can provide for automated sequencing that can be used to gather sequence information from a plurality of sequences in parallel, i.e., substantially simultaneously. In various embodiments of instruments and methods for sequencing, the target sequences can be arrayed or otherwise distributed on a substantially planar substrate, or plate, located in a flow cell, as will be discussed in more detail subsequently.

In FIG. 1, embodiments of an automated sequencing instrument 100 can have a sample processing unit 120 that comprises a moveable stage and a thermostatted flow cell. According to various embodiments of an automated sequencing instrument 100, a flow cell can comprise a chamber that has input and output ports through which fluid can flow. The flow of fluid can be controlled by the fluidic delivery and control unit 110, thereby allowing for the automated removal or addition of various reagents from moieties (e.g., templates, microparticles, analytes, etc.) located in the flow cell. According to various embodiments of instrument 100, a flow cell includes a location at which a substrate or plate, e.g. a substantially planar substrate or plate such as a glass slide, can be mounted so that fluid flows over the surface of the substrate or plate, and a window to allow illumination, excitation, signal acquisition, etc. using various embodiments of an optical unit 130. In various embodiments of next generation sequencing systems, moieties such as microparticles are typically arrayed or otherwise distributed on the substrate before it is placed within the flow cell.

In various embodiments of instrument 100, an optical unit 130 can comprise a source, a CCD camera, and a fluorescence microscope. It will be appreciated by one skilled in the art that in various embodiments of optical unit 130, substitutions of components can be made. For example, alternative image capture devices can be used. Additionally, data acquisition, analysis and control unit 140 provides control to properly sequence various components of unit 110-140 shown in FIG. 1, such as the pumps, stage, cameras, filters, temperature control and to annotate and store the image data. A user interface is provided to assist the operator in setting up and maintaining the instrument, and can include functions to position the stage for loading/unloading slides and priming the fluid lines. Display functions can be included, for example, to show the operator various running parameters, such as temperatures, stage position, current optical filter configuration, the state of a running protocol, etc. In various embodiments, data acquisition, analysis and control unit 140 also comprises an interface to the database to record tracking data such as reagent lots and sample IDs.

It will be appreciated by one skilled in the art that various embodiments of instrument 100 can be used to practice a variety of sequencing methods including both the ligation-based methods described herein and other solid phase sequencing methods including, for example, but not limited by, sequencing by synthesis methods. As is the case for the ligation-based sequencing methods, sequencing by synthesis can be done on templates immobilized directly in or on a semi-solid support, templates immobilized on microparticles in or on a semi-solid support, templates attached directly to a substrate, etc.

According to various embodiments of the present teachings, a set of controls can include a plurality of deterministic synthetic beads each having at least one synthetic nucleic acid sequence attached thereto.

In further embodiments, each synthetic bead has a plurality of the unique nucleic acid sequence attached thereto. By way of non-limiting example, the set of controls can comprise 64 types of beads, wherein each type of beads comprises multiple copies of a respective unique nucleic acid sequence. In at least one further embodiment, the nucleic acid sequence attached to each bead consists essentially of the unique nucleic acid sequence. For example, one synthetic bead in the set can comprise the sequence 5'-AAA-3' and another synthetic bead in the set can comprise the sequence 5'-AAT-3', or any one of the other 63 variations possible with a 3-base sequence in the example of a 64 bead set. A set of control beads can include a multiple copies of each of a plurality of synthetic beads comprising the unique nucleic acid sequences; in other words, each set can include plural groups of beads, with each bead in a group having the same unique synthetic nucleic acid sequence attached thereto.

In at least one embodiment, the number of synthetic nucleic acid sequences can be designed based on the number of bases covered by a probe sequence used in the sequencing technique. For example, for a probe sequence that covers 3 bases at a time, a group of 64 unique synthetic nucleic acid sequences can be designed. Likewise, for a probe sequence that covers 4 bases at a time, a group of 256 unique nucleic acid sequences can be used, and for a probe sequence that covers 5 bases at a time, a group of 1024 unique nucleic acid sequences can be used. Similarly, larger groups of unique nucleic acid sequences can be used for probe sequences that cover a greater number of bases. The number of bases covered by a probe sequence can be selected, for example, based on the complexity of the analysis and the level of accuracy desired. Those having ordinary skill in the art will appreciate that probe lengths of 2 or more bases can be used and the synthetic nucleic acid sequences designed accordingly. The following non-limiting embodiments and examples are described with respect to dibase probe sequences with 4 total dyes.

In at least one embodiment, each of the probe sequences can have at least one dye attached to provide a detectable signal. According to at least one embodiment, 4 dyes can be attached to probe sequences that probe 2 bases at a time. When 4 dyes are used for dibase sequences, each dye represents 1 of 4 different 2-base sequences. One skilled in the art would recognize that other numbers of dyes can be used based on the number of bases interrogated by each probe sequence and the total number of unique sequences in the control set.

Exemplary non-deterministic synthetic beads have been described in U.S. patent application Ser. No. 12/555,549, currently pending, entitled "METHODS AND SYSTEMS FOR NUCLEIC ACID SEQUENCING Validation, Calibration and Normalization," filed on Sep. 8, 2009, the entirety of which is hereby incorporated by reference. After the synthetic nucleic acids used in control sets in accordance with exemplary embodiments of the present teachings are designed, as explained in further detail below, the synthetic beads of the present teachings can be made in a similar manner as disclosed in U.S. patent application Ser. No. 12/555,549. For example, the synthetic control beads can be made by amplifying a nucleic acid sequence attached to a bead monoclonally using a PCR reaction. The bead density, i.e., the number of nucleic acids attached to each bead, can be controlled such that a control set comprising a full complement of beads can be obtained by pooling beads comprising each unique sequence.

In some embodiments, the set of controls can include a substrate or plate having a plurality of synthetic nucleic acid sequences attached on a surface of the substrate or plate. The synthetic nucleic acid sequences can be arranged in a set of distinct locations, with each location having one or more nucleic acids with a substantially identical sequence. Further, different locations may have different synthetic nucleic acid sequences attached thereto. In a particular embodiment, the set of distinct locations can include groups of locations, with each location in a group having the same unique synthetic nucleic acid sequence attached thereto.

Figure 3:
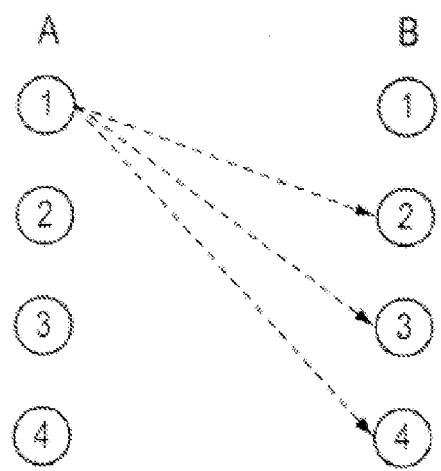
FIG. 3 is a schematic depiction of possible color transitions for an exemplary embodiment of a non-deterministic control set.
Figure 4A:
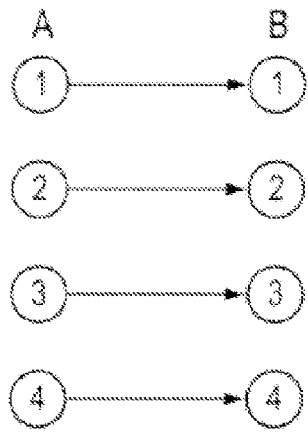
FIGS. 4A-4D is a schematic depiction of possible color transitions for an exemplary embodiment of a deterministic control set in accordance with the present teachings.
Figure 4B:
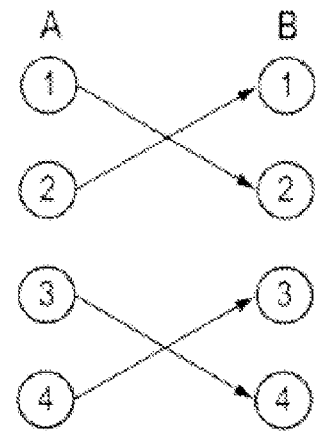
Figure 4C:
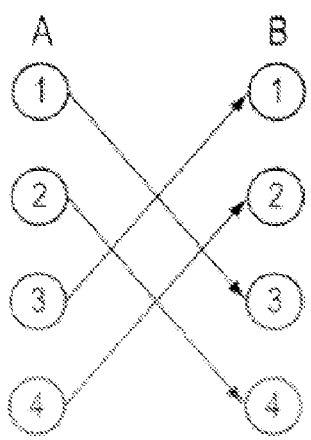
Figure 4D:
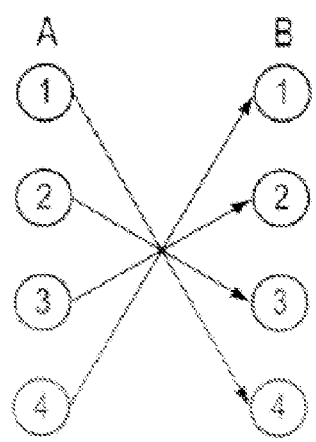

A schematic diagram of non-deterministic synthetic nucleic acid sequences is shown in FIG. 3. In FIG. 3, each of the circles represents a synthetic nucleic acid sequence that will exhibit one of four unique colors (numbered 1-4 for simplicity) after the completion of each sequencing cycle, such as a ligation cycle, a synthesis cycle, or the like. By exhibiting a color, those having ordinary skill in the art would understand that detection of the synthetic nucleic acid sequence will result in detection of a color, for example, due to a dye-labeled probe sequence being ligated to the complementary sequence of the synthetic nucleic acid sequence during a ligation cycle. In one embodiment described in U.S. patent application Ser. No. 12/555,549, synthetic sequences are designed such that the same color call would not be repeated in consecutive ligation cycles. In FIG. 3, the first column of circles represents each possible color in a ligation cycle $LC_n$. The next consecutive ligation cycle $LC_{n+1}$ is depicted by the second column of circles. For a non-deterministic synthetic control bead that is detected as color 1 in the ligation cycle $LC_n$, the same synthetic control bead will exhibit a color chosen from 2, 3, or 4 in the next consecutive ligation cycle $LC_{n+1}$. A color transition from color 1 in ligation cycle $LC_n$ to color 1 in ligation cycle $LC_{n+1}$ cannot occur for the non-deterministic synthetic control beads taught in U.S. patent application Ser. No. 12/555,549, incorporated by reference herein. However, the color call in ligation cycle $LC_{n+1}$ can be any one of the three other colors 2, 3, or 4. In a four-dye system that prohibits transitions of the same color, 12 of the possible 16 color transitions are available between consecutive ligation cycles. While 12 color transitions are available, all 12 color transitions will not necessarily be present between cycles.

FIGS. 4A-4D depicts the possible color transitions for a 4 dye system in a deterministic control set in accordance with the teachings herein. In such a deterministic control set, each of the 16 possible color transitions will appear in substantially equal probability for any consecutive ligation cycles. For example, in ligation cycle $LC_n$ if the color 1 is detected for a given synthetic sequence (with each numbered circle on the left representing a synthetic sequence having the designated color call at ligation cycle $LC_n$), color 1, 2, 3, or 4 can be detected for that synthetic sequence in ligation cycle $LC_{n+1}$. Therefore, all color transition properties can be represented. For example, in a 4-dye system, all 16 possible color transitions can be observed between consecutive ligation cycles.

Figure 5:
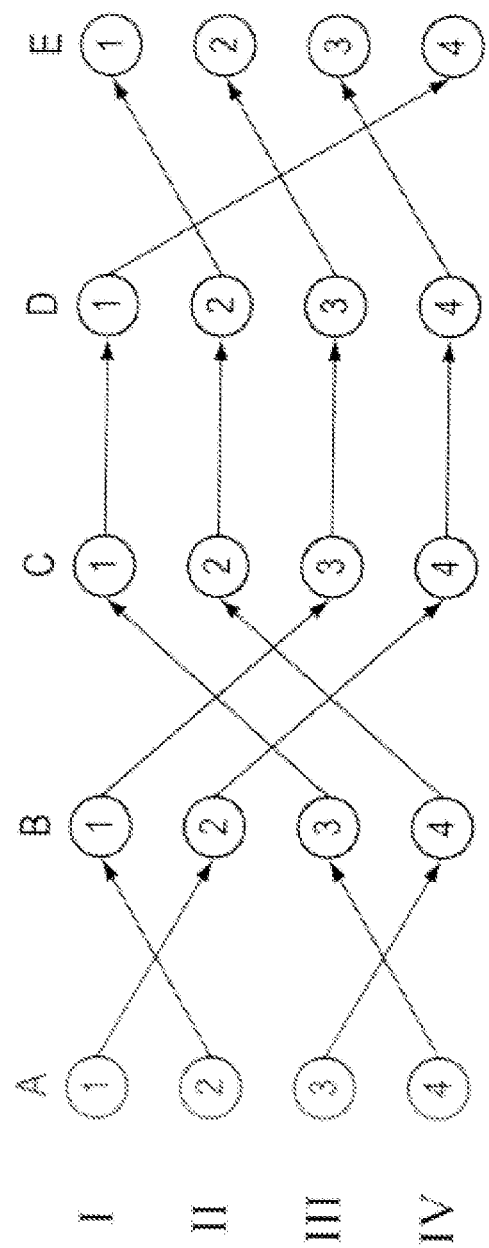
FIG. 5 is a schematic depiction of the color transitions of an exemplary embodiment of a control set for a series of ligation cycles in accordance with the present teachings.

An exemplary color transition sequence for a series of ligation cycles of one subset is depicted in FIG. 5. In FIG. 5, beads in row I exhibit color 1 in the first ligation cycle $LC_1$. In subsequent ligation cycles $LC_2$, $LC_3$, $LC_4$, and $LC_5$, the color transitions for row I will be from color 1 to color 2, from color 2 to color 4, from color 4 to color 4, and from color 4 to color 3, respectively (i.e., color 1→color 2→color 4→color 4→color 3). Beads in row II exhibit color transitions from color 2→color 1→color 3→color 3→color 2. Beads in row III exhibit color transitions from color 3→color 4→color 2→color 2→color 1. Beads in row IV exhibit a first color 4 and have color transitions from color 4→color 3→color 1→color 1→color 4. Therefore, each of the beads in rows I-IV in FIG. 5 follow a different color transition sequence. Other subsets of beads in each control set can follow different defined color transition sequences.

Subsets of beads or distinct locations can be determined in various ways according to embodiments of the present teachings. Because the transitions for each subset can be pre-defined, the color transitions are known and the identity of the beads in each subset can be determined by observing the color calls for the first 2 ligation cycles. In at least one other embodiment, each subset can be identified by an insertion of a set of unique sequences in a sequencing primer or adaptor. The detection of the sequence is performed using the fluorescently labeled nucleic acid oligonucleotide. For example, a 4-dye system can comprise 4 different insertion sequences that define the subsets.

According to at least one embodiment of the present teachings, the synthetic nucleic acids can be designed according to the following design criteria: 1) optionally, the number of subsets equals the number of uniquely colored dyes used in the probe sequences (e.g., 4 subsets when 4 dye colors are used); 2) pre-defined color transitions occur between consecutive ligation cycles for the set and/or each of the subsets; 3) all possible color transitions are observed between consecutive ligation cycles (e.g., 16 color transitions when 4 dyes are used); 4) complete set of possible 5-mer nucleic acid sequences within each window, e.g., a range of bases such as bases 41-45 of each nucleic acid sequence, equals the number of bases covered by each probe sequence (e.g., 1024 unique 5-mers in any 5-base window); and 5) minimizing the folding free energy and the amount of secondary structures with physics-based models, balancing the GC/AT contents of the sequences, and using sequences with the most consistent sequencing behavior. In at least one embodiment, the synthetic nucleic acid sequences are designed based on at least criteria 2-5 above.

In at least one exemplary embodiment, a control set can include 1024 unique synthetic nucleic acids and probe sequences having 1 of 4 dyes attached and covering 5 bases at a time can be used as the probes for each ligation cycle. The probe sequences can interrogate the last 2 bases of each 5-base sequence covered by the probe sequence (i.e., a dibase probe that is 5 bases long). The unique synthetic nucleic acid sequences can be designed such that every possible combination of 5 bases is present exactly once in each ligation cycle, which provides for 1024 unique sequences. Because 4 dyes are used to represent all 16 possible 2-base combinations, the 1024 unique sequences should be evenly represented by the 4 dye colors in subsets of 256 unique nucleic acid sequences each.

In at least one exemplary embodiment, a control set of unique synthetic nucleic acid sequences can be designed such that the color transitions between consecutive cycles are pre-defined. For example, if the first observed color is color 1, then the next observed color is color 3. If the next observed color is not color 3 (or other predetermined color), then it can be determined that a problem with the instrument, the workflow, the signal processing, and/or with the sample can exist.

According to at least one embodiment, each subset of the control set can follow different color transition rules (i.e., exhibit different color calls for consecutive ligation cycles). In the example shown in FIG. 5, for example, the color transition rule for subset I could be that color 1 should transition to color 2 in the next cycle $LC_2$, followed by color 4, then color 4, and then color 3 for cycles $LC_3$ through $LC_5$, respectively. The example shown in FIG. 5 illustrates 5 ligation cycles. The actual number of ligation cycles, however, will be different for each nucleic acid length. The color transition rule can repeat after each set of ligation cycles needed to complete the sequencing run, or the color transition rule can define the color transitions for the entire sequencing run. In at least one embodiment, all possible color transitions can be observed between all cycles for an entire control set. For example, the color transition rules can be defined such that each possible color transition is represented in each ligation cycle. Thus, if the first color call of a bead of one subset is 1 and the second color call is 2, none of the beads in the other subsets can exhibit the same transition from color 1 to color 2.

Figure 2A:
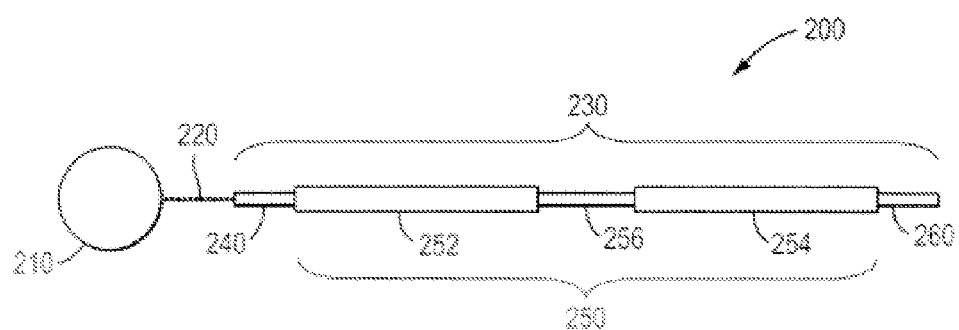
FIGS. 2A and 2B are schematic depictions of an exemplary embodiments of a synthetic control bead in accordance with the present teachings.

FIG. 2A schematically depicts a synthetic bead 200 according to at least one embodiment. Synthetic beads 200 include a bead 210 having a linker 220, which is a synthetic sequence for attaching a synthetic template 230 to the bead. The synthetic template 230 can include a first or P1 priming site 240, an insert 250, and a second or P2 priming site 260. The length of the linker 220 and synthetic template 230 can vary in length. For example, the length of the linker 220 can range from about 10 to about 100 bases, for example, from about 15 to about 45 bases, such as, for example, about 18 bases in length. Template 230, which comprises P1 240, insert 250, and P2 260, can also vary in length. In at least one embodiment, P1 240 and P2 260 can each range from about 10 to about 100 bases, for example, from about 15 to about 45 bases, such as, for example, about 23 bases in length. Insert 250 can comprise a first synthetic tag sequence 252, a second synthetic tag sequence 254, and an internal adapter 256 located between the first and second tag sequences 252, 254. The first and second tag sequences 252, 254 can have a length ranging from about 2 bases to about 20,000 bases, such as, for example, about 60 bases. The first and second tag sequences 252, 254 can be the same sequence or different sequences. The first and second tag sequences 252, 254 can comprise a different number of bases or the same number of bases. The internal adapter 256, which can be common to all template sequences in a control set, can have a length ranging from about 10 to about 100 bases, for example, from about 15 to about 45 bases, such as, for example, about 36 bases.

In at least one embodiment, the first and second tag sequences 252 and 254, can comprise synthetic nucleic acid sequences designed according the embodiments described above. Each control set comprises a plurality of synthetic beads 200 comprising different inserts 250. For example, in at least one embodiment, a control set can comprise synthetic beads comprising at least 1024 unique inserts 250. One of ordinary skill in the art would recognize that the number of bases in each unique insert sequence 250 can be selected based on several criteria, including, but not limited to, the desired accuracy of the control set, the complexity of the sample being studied, etc. The synthetic nucleic acid sequences, once designed, can be produced and attached to beads according to the methods described in U.S. patent application Ser. No. 12/555,549, incorporated by reference herein.

In various exemplary embodiments, additional internal adapters and/or tag sequences can be used. For example, an insert can comprise 3 or more tag sequences and 2 or more internal adapters, respectively, in an alternating pattern. Various other types of sequence patterns can be utilized for the synthetic nucleic acid sequences depending on the desired application.

In at least one embodiment, the nucleic acid sequence can not contain an internal adapter and comprise a single tag sequence. In such embodiments, the synthetic nucleic acid sequences can resemble nucleic acid sequences of a fragment library.

In at least one exemplary embodiment, the internal adapter can comprise a primer sequence, which can be an additional primer in a PCR amplification process.

According to various exemplary embodiments of synthetic beads, the design features of the synthetic beads, as well as the methods of preparation of synthetic beads ensuring batch-to-batch reproducibility, as described in U.S. patent application Ser. No. 12/555,549, incorporated herein by reference, make synthetic beads desirable controls for instrument validation, calibration, and normalization, as well as for probe chemistry quality control.

Figure 2B:
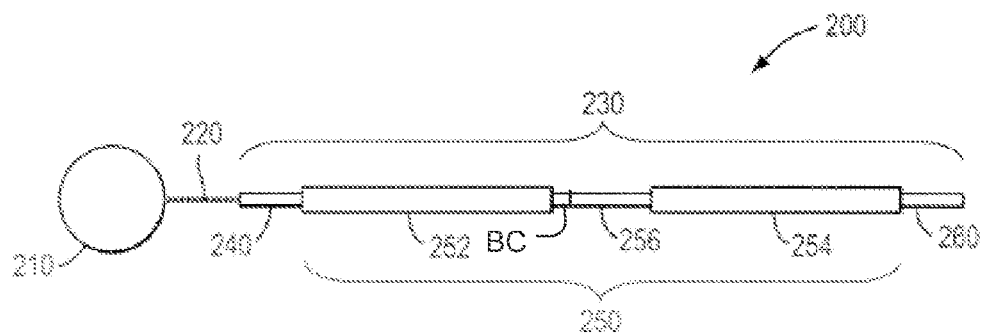

In other exemplary embodiments, synthetic bead 200 can further comprise a control identification sequence CID. As illustrated in FIG. 2B, control identification sequence CID is positioned between the first tag sequence 252 and the internal adapter 256. In another embodiment, control identification sequence CID can be positioned between P1 priming site 240 and the first tag sequence 252, or between second tag sequence 254 and P2 priming site 260. A person of ordinary skill would recognize other locations for the control identification sequence CID in other embodiments.

According to at least one embodiment, the position of the control identification sequence CID can be selected based on the length of the first or second tag and/or to avoid any potential sequencing bias. For example, the signal to noise can decrease as additional ligation cycles are performed. When signal to noise may be an issue, the control identification sequence CID can be positioned adjacent P1 priming site 240 to avoid potential errors due to diminished signal to noise. In situations where the signal to noise ratio may not vary significantly from early ligation cycles to later ligation cycles, the control identification sequence CID can be placed adjacent to the internal adapter 256.

In at least one embodiment, the position of the control identification sequence CID can be selected to avoid potential sequencing bias. For example, some template sequences may interact differently with a probe sequence used during the sequencing experiment. Placing the control identification sequence CID between the priming site and the tag sequence can affect the sequencing results for the tag. Positioning the control identification sequence CID after the tag sequence can decrease sequencing errors due to bias. One of ordinary skill in the art would recognize that the position of the control identification sequence CID can be affected by or affect the sequencing process and accordingly can chose the position that best achieves the desired results based on the conditions of the sequencing process.

According to at least one embodiment of the present teachings, the control identification sequence (and the tag sequence) can be designed to optimize the control identification sequence's observed performance in a sequencing process. In at least one embodiment, the control identification sequence can be designed to avoid sequences that may be problematic. For example, repetitive sequences can be avoided, such as 5'GGGG-'3 and 5'-CCCC-3'. Other sequences that can be avoided include those that result in repetitive color calls. For example, sequences that result in the same color call 4 or more times can be avoided. Other sequences that can be avoided include A-T rich and G-C rich sequences, such as, for example, {A,T}5 and {G,C}5. According to at least one embodiment, the control identification sequence can be designed based on the fidelity with which it is sequenced. For example, the fidelity with which a control identification sequence can be sequenced can be estimated based on empirical measurements with sequencing probes. The sequencing fidelity may be affected, for example, by sequencing bias of certain nucleic acid sequences. In embodiment wherein the control identification sequence is designed to have high fidelity, the probability of the nucleic acid barcode to be correctly sequenced and thus identified can be improved. In at least one embodiment, the probability that all bases in a control identification sequence are sequenced correctly can be at least 82%. An exemplary control identification sequence can include 5'-CCA AGG GAG GAC TGA TCC-3' (SEQ ID NO: 1). Another exemplary control identification sequence can include 5'-CCA AGG GAG GAC TGA TCC GCC TTG GCC GTA CAG CAG-3' (SEQ ID NO: 2).

The synthetic beads according to the various embodiments of the present teachings can be used in each of the methods described in U.S. patent application Ser. No. 12/555,549, incorporated herein by reference. When using the synthetic control beads, however, real-time monitoring of instrument quality or quality control can be possible due to the deterministic nature of the synthetic control beads of the present teachings.

Figure 6:
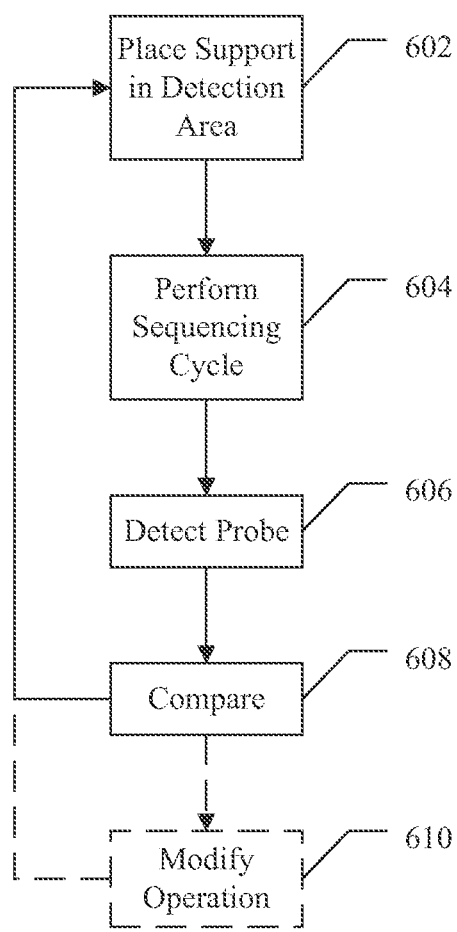
FIG. 6 is a flow diagram illustrating an exemplary embodiment of a method of utilizing the synthetic nucleic acid sequences in accordance with the present teachings.

FIG. 6 illustrates an exemplary method of utilizing the synthetic nucleic acid sequences. At 602, a control set can be placed in the detection area of a sequencing instrument, such as instrument 100. The control set can include a plurality of synthetic nucleic acid sequences according to aspects of the present disclosure. In a particular embodiment, a nucleic acid sample can be placed in the detection area along with the control set.

At 604, a sequencing cycle can be performed. For example, a ligation sample can be performed to attach a dye-labeled probe to the synthetic nucleic acid sequences and the nucleic acid sample (when present). In another example, the sequencing cycle may include synthesizing an additional portion of a complementary nucleic acid strand to attach the dye-labeled probe. At 606, the sequencing instrument can detect the probe attached to each of the nucleic acid sequences, and at 608, the detected probe attached to the synthetic nucleic acid sequences can be compared to the predefined pattern of detectable signals used to design the synthetic. The instrument can perform additionally sequencing cycles, as illustrated at 604.

Optionally, the operation of the instrument can be modified based on the comparison, as illustrated at 610. For example, when an error is identified, such as the detected probe attached to a synthetic nucleic acid sequence does not match the predefined pattern of detectable signals, the operation can be paused from proceeding to determine the cause of the error. In another example, a signal to noise ratio for the synthetic nucleic acid sequences can be compared to a prior sequencing cycle, and the data can be adjusted accordingly to account for the increased noise and/or decreased signal during the experiment.

According to various exemplary embodiments of the present teachings, control sets of the deterministic synthetic beads described above can be used to validate sequencing instruments, for example, for verifying instrument quality (IQ), and for validating sequencing data. In at least one embodiment, instrument quality can be determined while a sequencing experiment is being performed; in other words in real-time or "on-the-fly." Because the color transitions for each subset of synthetic beads is known, any deviations from the expected and predefined color transitions can be construed as an error. For example, a control set of beads can be run with an unknown sample. If the expected color transitions do not appear in control beads, it can indicate an error with the unknown sample, the instrument or with the data collected. Therefore, when an error is observed, the experiment (e.g., the sequencing run) can be paused from proceeding to determine the cause of the error. The ability to observe the quality of the experiment as it is being run can reduce the amount of time and resources required to perform nucleic acid sequencing. Furthermore, upon completion of the experiment, the control set can be identified based on the control identification sequence and can be excluded from further analysis of the unknown sample.

According to at least one embodiment, the deterministic synthetic beads can also be used to improve the signal to noise (S/N) ratio present in sequencing data. The signal to noise ratio during sequencing runs typically decreases as the experiment is being carried out. For example, the signal to noise ratio at the beginning of a sequencing run can be much greater than the signal to noise ratio at the end of the experiment. The degradation of the signal-to-noise ratio can originate from various sources, including a non-specific ligation reaction, image quality degradation due to lower reaction efficiency, and/or residual fluorescent signal from previous cycles. Because the color transitions are known for deterministic synthetic beads, the signal from one of the unique dyes at each ligation cycle can be compared to the signal from the dye at the previous ligation cycle. By comparing the signal of the later cycle that has a lower S/N ratio with the signal of the earlier cycle which has a higher S/N ratio, the data can be adjusted accordingly to account for the increased noise and/or decreased signal during the experiment.

Although the various embodiments describe beads as the solid support on which the synthetic nucleic acid sequences are attached, other solid supports can also be utilized, such as, for example, microparticles, micro-arrays, slides, etc. Additionally, the beads can comprise any known material known for such use, including polymeric and inorganic materials, as well as paramagnetic and non-paramagnetic materials. The selection of the appropriate solid support would be within the capabilities of one of ordinary skill in the art to determine based on the sequencing platform used, the materials used to carry out the study, and any other factor that can influence the running of the experiment.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

While the principles of the present teachings have been described in connection with specific embodiments of synthetic beads and sequencing platforms, it should be understood clearly that these descriptions are made only by way of example and are not intended to limit the scope of the present teachings or claims. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalents.

What is claimed is:

1. A method of processing nucleic acid sequencing data during a nucleic acid sequencing experiment, comprising:
   placing a set of control solid supports each having a plurality of synthetic nucleic acid sequences attached thereto in a detection area of a nucleic acid sequencing instrument, wherein the set of control solid supports comprises plural groups of control solid supports that each have the same synthetic nucleic acid sequences attached thereto and wherein the synthetic nucleic acid sequences are designed such that the synthetic nucleic acid sequences produce a predefined pattern of observable signals during the nucleic acid sequencing experiment;
   placing a template solid support having a nucleic acid sample to be sequenced attached thereto in a detection area of the nucleic acid sequencing instrument along with the set of control solid supports;
   performing a first ligation cycle to attach dye-labeled probe sequences to the synthetic nucleic acid sequences attached to the control solid supports and to the nucleic acid sample attached to the template solid support;
   detecting the dye-labeled probes attached to each of the synthetic nucleic acid sequences and the nucleic acid sample after the first ligation cycle;
   performing a second ligation cycle to attach a dye-labeled probe sequences to the synthetic nucleic acid sequences attached to the control solid supports and to the nucleic acid sample attached to the template solid support;
   detecting the dye-labeled probes attached to each of the synthetic nucleic acid sequences and the nucleic acid sample after the second ligation cycle;
   comparing an intensity of the detected dye-labeled probes attached to the synthetic nucleic acid sequences after the first ligation cycle with an intensity of the detected dye-labeled probes attached to the synthetic nucleic acid sequences after the second ligation cycle; and
   adjusting an intensity of the detected dye-labeled probes attached to the nucleic acid sample after the second ligation cycle based on the compared intensities,
   wherein the predefined pattern of observable signals comprises transitions based on 12 of the 16 color transitions available when using 4 colors between consecutive ligation cycles while prohibiting transitions of the same color.

2. The method of claim 1, further comprising repeating performing a ligation cycle, detecting the-dye-labeled probe, comparing the intensities, and adjusting the intensity of the detected dye-labeled probe attached to the nucleic acid sample based on the compared intensities.

3. The method of claim 1, further comprising identifying the synthetic nucleic acid sequences based on a presence of a control identification sequence.

4. The method of claim 3, further comprising excluding the synthetic nucleic acid sequences from data corresponding to the nucleic acid sample.

5. The method of claim 1, wherein the synthetic nucleic acid sequence comprised in any one of the plural groups is different than the synthetic nucleic acid sequences comprised in the other ones of the plural groups.

6. The method of claim 1, wherein the plurality of synthetic nucleic acid sequences in the set of control solid supports comprises every possible variation of a set-length sequence.

7. The method of claim 1, wherein the plurality of synthetic nucleic acid sequences in the set of control solid supports comprises a set of 64 synthetic nucleic acid sequences comprising each possible combination of a 3 base sequence.

8. The method of claim 1, wherein the plurality of synthetic nucleic acid sequences in the set of control solid supports comprises a set of 256 synthetic nucleic acid sequences comprising each possible combination of a 4 base sequence.

9. A method of processing nucleic acid sequencing data during a nucleic acid sequencing experiment, comprising:
   placing a set of control solid supports each having a plurality of synthetic nucleic acid sequences attached thereto in a detection area of a nucleic acid sequencing instrument, wherein the set of control solid supports comprises plural groups of control solid supports that each have the same synthetic nucleic acid sequences attached thereto and wherein the synthetic nucleic acid sequences are designed such that the synthetic nucleic acid sequences produce a predefined pattern of observable signals during the nucleic acid sequencing experiment;
   placing a template solid support having a nucleic acid sample to be sequenced attached thereto in a detection area of the nucleic acid sequencing instrument along with the set of control solid supports;
   performing a first ligation cycle to attach dye-labeled probe sequences to the synthetic nucleic acid sequences attached to the control solid supports and to the nucleic acid sample attached to the template solid support;
   detecting the dye-labeled probes attached to each of the synthetic nucleic acid sequences and the nucleic acid sample after the first ligation cycle;
   performing a second ligation cycle to attach a dye-labeled probe sequences to the synthetic nucleic acid sequences attached to the control solid supports and to the nucleic acid sample attached to the template solid support;

detecting the dye-labeled probes attached to each of the synthetic nucleic acid sequences and the nucleic acid sample after the second ligation cycle;

comparing an intensity of the detected dye-labeled probes attached to the synthetic nucleic acid sequences after the first ligation cycle with an intensity of the detected dye-labeled probes attached to the synthetic nucleic acid sequences after the second ligation cycle; and adjusting an intensity of the detected dye-labeled probes attached to the nucleic acid sample after the second ligation cycle based on the compared intensities, wherein the plurality of synthetic nucleic acid sequences in the set of control solid supports comprises a set of 1024 synthetic nucleic acid sequences comprising each possible combination of a 5 base sequence.

10. The method of claim 1, wherein the groups of control solid supports comprise beads having a plurality of synthetic nucleic acid sequences attached thereto.

11. The method of claim 1, wherein the groups of control solid supports comprise one or more of (i) nucleic acid sequences provided as a fragment library, (ii) nucleic acid sequences provided as a mate-pair library, and (iii) nucleic acid sequences provided as analogous synthetic libraries.

12. The method of claim 1, wherein the groups of control solid supports comprise one or more of (i) nucleic acid sequences provided as a template comprising multiple inserts and multiple internal adapters, and (ii) nucleic acid sequences including concatenates.

13. The method of claim 1, wherein the predefined pattern of observable signals comprises predefined color transitions between consecutive ligation cycles.

14. The method of claim 9, wherein the predefined pattern of observable signals comprises color transitions from a first color to a second color, from the second color to a fourth color, from the fourth color to the fourth color, and from the fourth color to a third color.

15. The method of claim 9, wherein the predefined pattern of observable signals comprises color transitions from a second color to a first color, from the first color to a third color, from the third color to the third color, and from the third color to a second color.

16. The method of claim 9, wherein the predefined pattern of observable signals comprises color transitions from a third color to a fourth color, from the fourth color to a second color, from the second color to the second color, and from the second color to a first color.

17. The method of claim 1, further comprising identifying an error when a detected intensity in the comparison does not match with the predefined pattern of observable signals, and pausing operation of the nucleic acid sequencing instrument to determine a cause of the identified error.

18. The method of claim 1, further comprising comparing a signal to noise ratio for the synthetic nucleic acid sequences to a prior sequencing cycle.

19. The method of claim 18, comprising adjusting intensities based on the signal to noise ratio comparison to account for an increased noise and/or decreased signal during the sequencing experiment.

* * * * *